US007052515B2

(12) United States Patent
Simonson (10) Patent No.: US 7,052,515 B2
(45) Date of Patent: May 30, 2006

(54) VERTEBRAL IMPLANT WITH DAMPENING MATRIX ADAPTED FOR POSTERIOR INSERTION

(76) Inventor: Rush E. Simonson, 18105 Turtle Beach Way, Tampa, FL (US) 33647

(*) Notice: Subject to any disclaimer, the term of this patent is extended or adjusted under 35 U.S.C. 154(b) by 219 days.

(21) Appl. No.: 10/449,733

(22) Filed: May 30, 2003

(65) Prior Publication Data
US 2004/0181284 A1 Sep. 16, 2004

Related U.S. Application Data

(63) Continuation-in-part of application No. 10/021,319, filed on Dec. 7, 2001, now Pat. No. 6,572,653.

(51) Int. Cl.
*A61F 2/44* (2006.01)
(52) U.S. Cl. .................................. 623/17.13
(58) Field of Classification Search ... 623/17.11–17.16
See application file for complete search history.

(56) References Cited

U.S. PATENT DOCUMENTS

| 4,349,921 | A | | 9/1982 | Kuntz |
| 5,401,269 | A | * | 3/1995 | Buttner-Janz et al. ... 623/17.15 |
| 5,458,642 | A | * | 10/1995 | Beer et al. ............... 623/17.13 |
| 5,824,093 | A | | 10/1998 | Ray et al. |
| 6,033,429 | A | | 3/2000 | Magovern |
| 6,227,266 | B1 | * | 5/2001 | Moore et al. ............... 141/392 |
| 6,395,032 | B1 | * | 5/2002 | Gauchet .................. 623/17.12 |
| 6,423,065 | B1 | | 7/2002 | Ferree |
| 6,533,817 | B1 | | 3/2003 | Norton et al. |

FOREIGN PATENT DOCUMENTS

WO   WO00/35386   *  6/2000

OTHER PUBLICATIONS

U.S. Appl. No. 10/434,931, filed May 2003, Ferree.*
Viscogliosi Bros., LLC, Artificial Discs: The Largest Growth Opportunity in Spine, Artificial Disc: Market Potential & Technology Update, 1999.

* cited by examiner

*Primary Examiner*—Eduardo O. Robert
*Assistant Examiner*—Michael J. Araj
(74) *Attorney, Agent, or Firm*—Townsend and Townsend and Crew LLP; Guy W. Chambers (57) ABSTRACT

Disclosed is an endoprosthetic implant for a human spinal disc. The structure of the implant allows it to be inserted posteriorly. This insertion is accomplished by performing a partial discectomy in the affected region. An intervertebral space is then created by removing the fibrocartilage between the facing surfaces of adjacent vertebrae. The implant is then inserted into the intervertebral space. The implant is thus adapted to replace damaged or worn intervertebral discs. Furthermore, the structure of the implant, and its posterior insertion, alleviate most spinal pathologies.

10 Claims, 9 Drawing Sheets

VERTEBRAL IMPLANT WITH DAMPENING MATRIX ADAPTED FOR POSTERIOR INSERTION

RELATED APPLICATION DATA

This application is a continuation-in-part of application Ser. No. 10/021,319 filed Dec. 7, 2001, now U.S. Pat. No. 6,572,653, and entitled "Vertebral Implant Adapted for Posterior Insertion," the contents of which are incorporated herein by reference in its entirety for all purposes.

BACKGROUND OF THE INVENTION

1. Field of the Invention

This invention relates to an endoprosthesis to replace an intervertebral disc. More particularly, the present invention relates to an endoprosthetic implant that is specifically designed to be inserted posteriorly.

2. Description of the Background Art

The human spine is made up of twenty-four stacked segments called vertebrae. Between adjacent vertebrae are small fibrocartilage cushions called intervertebral discs. These discs act as shock absorbers between adjacent vertebrae and permit the spinal column to bend. As bodily forces are transmitted along spine, an individual disc can often encounter hundreds of pounds of force. Spinal forces are also transmitted by way of inferior and superior articular processes that contact each other at facet joints. Intervertebral discs and facet joints are the two spinal mechanisms by which most spinal forces are transmitted. Consequently, most spinal pathology occurs at these locations.

For example, the fibrocartilage in the intervertebral discs often becomes worn or damaged through wear, age and/or disease. This damage limits spinal movements and can also result in pain as nerves become pinched and swollen. Damaged fibrocartilage, in turn, increases the pressure that is otherwise encountered by the facet joint adjacent the disc. This causes a premature wearing of the bone that makes up the joint. Again, limited spinal movement and pain result.

One of the oldest methods of repairing damaged intervertebral discs involves fusing adjacent vertebrae by way of a bone graft. Such methods, however, have serious drawbacks in that the resulting fused vertebrae limit the overall movement of the spine. Furthermore, once two vertebrae are fused, the pressures encountered by adjacent healthy discs is increased. This dramatically increases the likelihood that such healthy discs may become damaged and worn. Thus, the fusing of vertebrae often propagates the malady it seeks to cure.

Prosthetics are also employed to alleviate damaged intervertebral discs. This involves the removal of damaged fibrocartilage. The fibrocartilage is then replaced by an implant, typically formed from an elastomeric or an elastomeric composite. Prosthetic implants have the benefit of providing a more full range of spinal movement over fusion processes. Nonetheless, the elastomerics typically wear out over the life of the prosthetic. As a result additional medical procedures are required to replace the worn out prosthetic. Even prior to wearing out, elastomerics may simply wear unevenly, whereby the prosthetic provides an uneven resilient force between the vertebrae. This causes nerves to become pinched and swollen. Absent any type of wearing, elastomerics do not provide a cushioning effect that is equivalent to naturally occurring fibrocartilage. Forces not absorbed by the elastomeric are then transferred to the adjacent facet joint. This results in premature wearing of the joint.

An example of a synthetic intervertebral disc is disclosed by U.S. Pat. No. 5,458,642 to Beer, et al. Beer discloses the use of a synthetic intervertebral disc for implantation in the human body. The synthetic disc includes a polymeric core that is inserted between two plates. Spring means are included in addition to the polymeric core. Each of the plates includes a tab that is secured to a vertebrae via a screw.

Additionally, U.S. Pat. No. 6,231,609 to Mehdizadeh discloses a disc replacement prosthesis. The prosthesis includes screw threads which engage the vertebrae. A vertical stiffness is obtained from a series of coil springs affixed between upper an lower rigid members. The coil springs also provide assistance in resisting shear forces.

U.S. Pat. No. 5,556,431 to Büttner-Janz discloses an intervertebral disc endoprosthesis. The prosthesis includes two plates intermediate which a prosthesis core is included. The prosthesis core is made from a polyethylene. Bone screws are utilized in securing the two plates.

U.S. Pat. No. 5,824,093 to Ray discloses a prosthetic spinal disc nucleus employing a hydrogel core surrounded by a constraining jacket.

Finally, U.S. Pat. No. 6,156,067 to Bryan, et al discloses a spinal disc endoprosthesis with concave surfaces. A resilient body is included intermediate the two surfaces.

Although each of the above-referenced inventions achieves its individual objective they all suffer from common problems. Namely, none of the background art discloses an endoprosthesis which is specifically designed to be inserted posteriorly to thereby eliminate the most common source of spinal pathology.

SUMMARY OF THE INVENTION

It is therefore one of the objectives of this invention to provide an intervertebral disc endoprosthesis which is specifically adapted to be inserted posteriorly.

It is also an object of this invention to provide an intervertebral endoprosthesis which utilizes a mechanical spring to achieve a longer wear life and accommodate increased intervertebral forces.

Still another object of this invention is to provide an endoprosthesis which substantially eliminates most posterior spinal pathology.

Yet another object of this invention is to provide an endoprosthesis which eliminates the need for facet joints.

These and other objectives are accomplished by providing a vertebral implant adapted for posterior insertion and designed to replace the fibrocartilage between the facing surfaces of adjacent superior and inferior lumbar vertebrae. The implant includes two pairs of hydroxyapatite coated superior and inferior supports. Each support includes plate and lip portions. The lip portion is formed at a right angle to the plate portion. In the case of the inferior support the lip portion is offset to one side. The plate portion of each support further includes a plurality of teeth, a retainer, and a pair of tapering side edges. Each plate portion is received within a channel formed within one of the facing surfaces of the superior or inferior vertebrae such that the lip portions abut the posterior edge of the vertebrae. In the case of the inferior support, the offset lip accommodates a vertebral pedical.

The implant additionally includes a pair of springs. Each spring is formed from a plurality of oblong tapered coils. Each spring is positioned between the side edges of opposing superior and inferior supports with the position of the spring being fixed by the opposing retainers. Each spring has an axial force under compression that functions to drive the teeth of the opposing superior and inferior supports into the facing surfaces of the adjacent vertebrae.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

The present invention relates to an endoprosthetic implant for a human spinal disc. The structure of the implant allows it to be inserted posteriorly. This insertion is accomplished by performing a partial discectomy in the affected region. An intervertebral space is then created by removing the fibrocartilage between the facing surfaces of adjacent vertebrae. The implant is then inserted into the intervertebral space. The implant is thus adapted to replace damaged or worn intervertebral discs. Furthermore, the structure of the implant, and its posterior insertion, alleviate most spinal pathologies. The implant of the present invention, and the manner in which it is employed, are described in fuller detail hereinafter.

Figure 1:
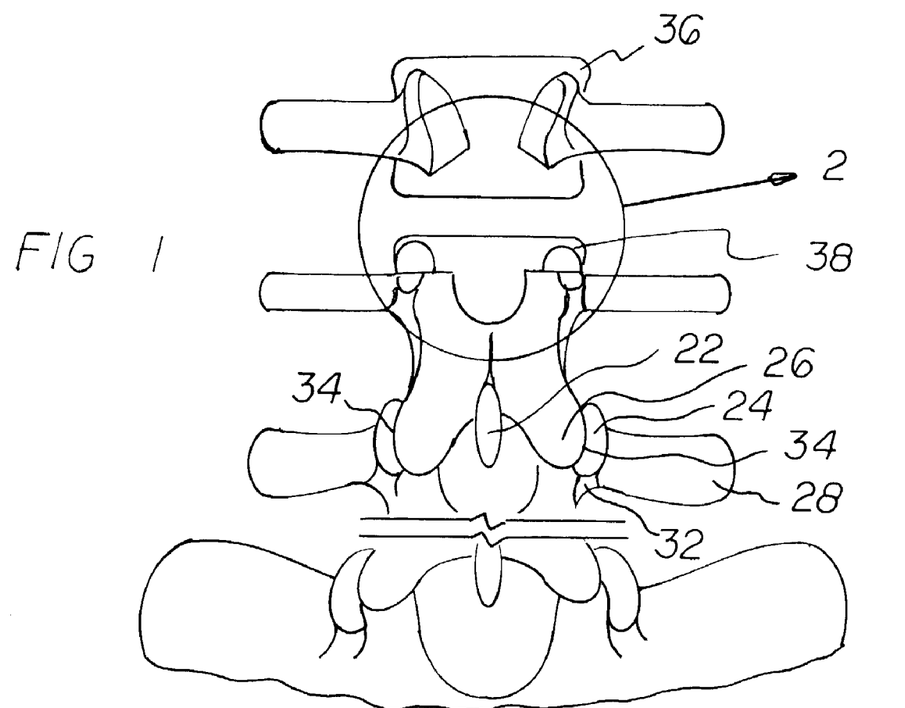
FIG. 1 is a posterior view of the lumbar region of a human spine.

With reference now to FIG. 1, a posterior view of the lumbar region of a human spine is depicted. The implant of the present invention 20 is specifically adapted for insertion between adjacent vertebrae in this lumbar region, specifically vertebrae L3 through S1. FIG. 1 illustrates some spinal anatomy including: the spinous process 22; the superior and inferior articular process (24 and 26, respectively); the transverse process 28; pedicals 32 and facet joints 34. FIG. 1 also illustrates a dissected area with the spinous process 22 and superior and inferior articular processes (24 and 26) removed. This discectomy allows for the insertion of the implant 20 of the present invention in a manner more fully described hereinafter.

Figure 2:
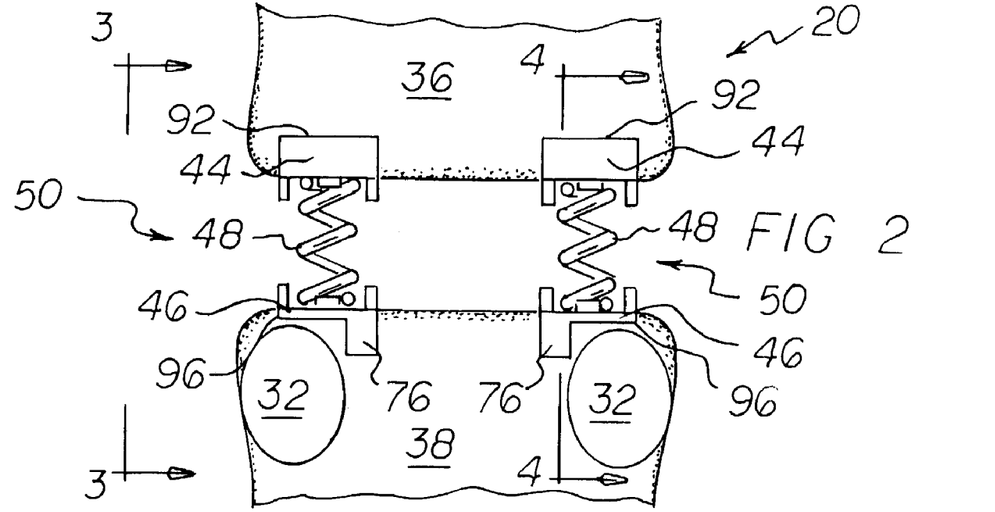
FIG. 2 is a detailed illustration taken from FIG. 1.
Figure 3:
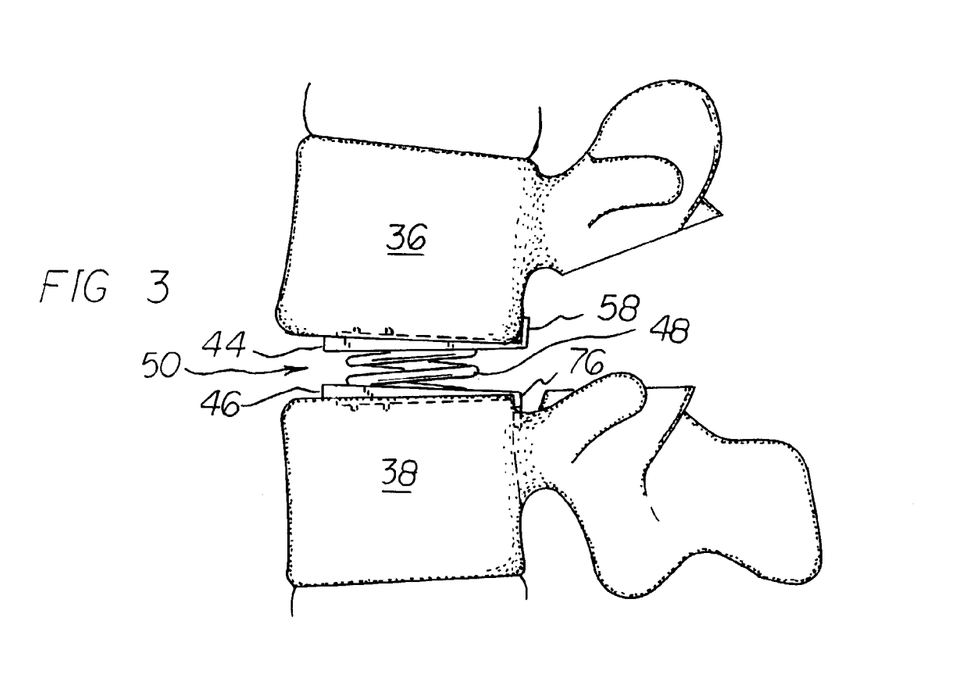
FIG. 3 is a side elevational view of the implant of the present invention fully inserted and is taken from line 3—3 of FIG. 2.

FIG. 2 illustrates the implant 20 positioned between facing surfaces of adjacent superior and inferior lumbar vertebrae (36 and 38, respectively). The implant 20 includes: an upper, or superior, pair of supports 44; a lower, or inferior, pair of supports 46; and two springs 48. As illustrated, each spring 48 is positioned between aligned opposing superior and inferior supports (44 and 46). Thus, an individual support column 50 is defined by a superior and inferior support (44 and 46) interconnected by a spring 48. The preferred form of the implant includes two support columns 50. However, the use of other numbers of columns, such as one or three, is within the scope of the present invention.

Figure 4:
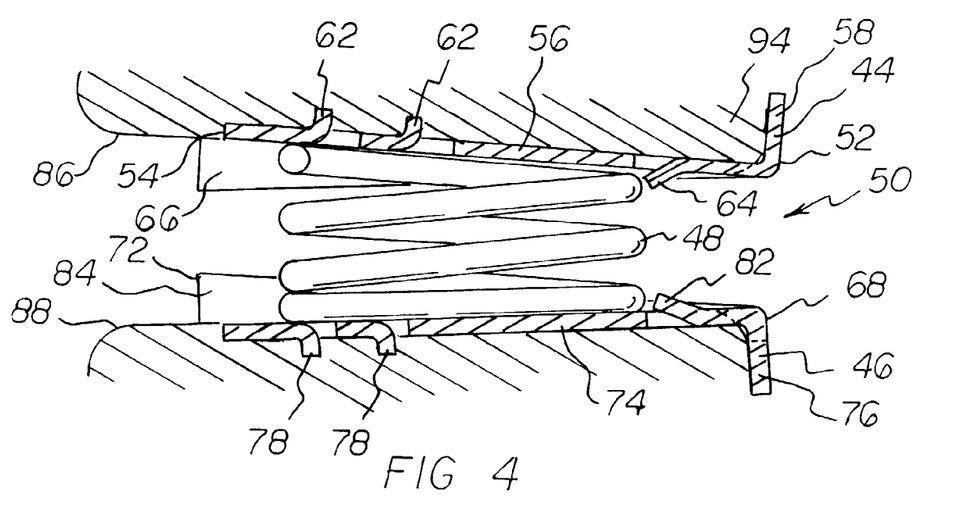
FIG. 4 is a cross-sectional view taken from line 4—4 of FIG. 2.

Each superior support 44 is defined by: first and second ends (52 and 54); a cantilevered plate portion 56; and a lip portion 58. The plate portion 56 is cantilevered with the first end 52 being integral with the lip portion 58 and the second end 54 being free. This arrangement allows the plate 56 to pivot with respect to the sides of the support. With reference now to FIG. 4, the relationship between the lip and plate portion (58 and 56) of a superior support 44 is depicted. Specifically, in the preferred embodiment, the lip portion 58 is formed at generally a right angle to the plate portion 56 at a first end 52 of the support 44. However, the exact angle between the lip portion 58 and the plate portion 56 varies due to the cantilevered nature of the plate. With continuing reference to FIG. 4, the teeth 62 of the plate portion 56 are depicted. These teeth 62 are formed by partially perforating the plate 56 to create protrusions which rise above the planer surface of the surrounding support 44. The teeth are preferably formed a 90 degree angle with the plate portion 56. The teeth 62 enable support 44 to engage the vertebral body in a manner more fully described hereinafter. Thus, although the teeth 62 have been described as perforations, they could be formed in a variety of different ways. For example, the teeth 62 could take the form of sharpened protrubences that are fixed to an outer surface of the plate 56, such as by welding. Additionally, the teeth 62 can be arranged in a number of different positions, other than the aligned orientation depicted. In the unbiased state of plate 56, the bottom of teeth 62 are flush with the bottom edge of the support 44 (note FIG. 6). The plate 56 further includes a retainer 64 formed in a manner similar to the teeth 62. Again, the retainer 64 is formed by perforating the plate portion 56 to create a raised protrusion. The retainer 64 functions in constraining the spring 48 positioned between the facing supports (44 and 46). Thus, the teeth 62 are raised in a direction opposite to the direction in which the retainer 64 is raised. That is, the teeth 62 are raised in the same direction of the lip 58, and the retainer 64 is raised in the opposite direction.

Figure 5:
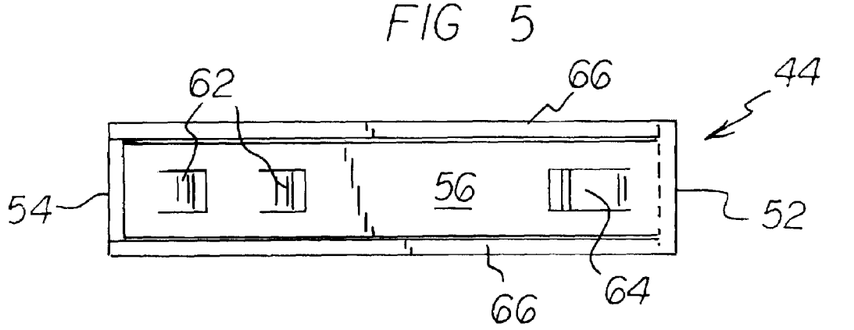
FIG. 5 is a top plan view of the superior support.
Figure 6:
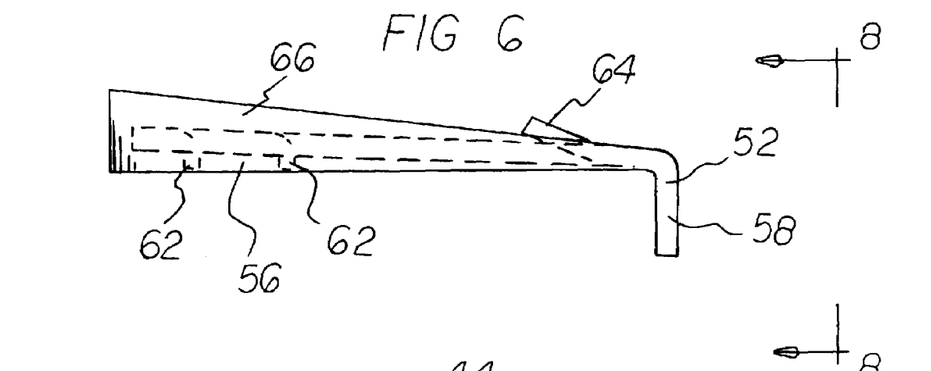
FIG. 6 is a side elevational view of one of the superior supports.
Figure 7:
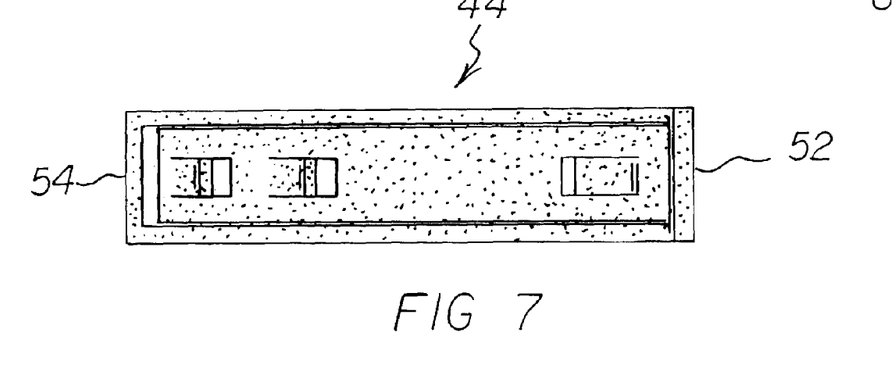
FIG. 7 is a bottom plan view of one of the superior supports.

FIGS. 5 through 7 are more detailed showings of the superior supports 44. As can be appreciated from these figures, the superior supports 44 further include raised side edges 66 which taper along the length of the support 44. That is, the side edges 66 are taller at the second end 54 of the support and taper toward the first end 52 of the support until the edges are planar with the plate portion 56. The raised side edges 66, along with the retainer 64, function in locking the spring 48 into position between opposing supports (44 and 46). Furthermore, due to the cantilevered nature of the plate 56, the side edges 66 are not connected with the edges of the plate 56.

With reference now to FIG. 4, the lower, or inferior supports 46, are described. In most respects, the inferior supports 46 are identical to the superior supports 44. That is, the inferior supports 46 are each defined by a first and second end (68 and 72), a cantilevered plate portion 74, and a lip portion 76. Again, the lip portion 76 is generally formed at a right angle to the plate portion 74 at the first end 68 of the support 46. Furthermore, the plate portion 74 includes a plurality of teeth 78 and a retainer 82, both of which are formed in the manner described in association with the superior support 44. Each of the inferior supports 46 similarly include raised side edges 84 which taper from the second 72 to the first end 68 of the support 46.

Figure 8:
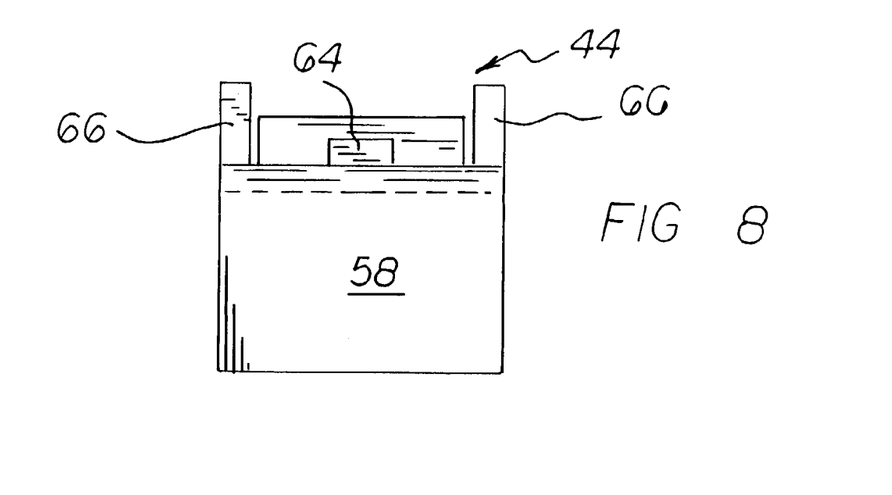
FIG. 8 is an end view taken along line 8—8 of FIG. 6.
Figure 9:
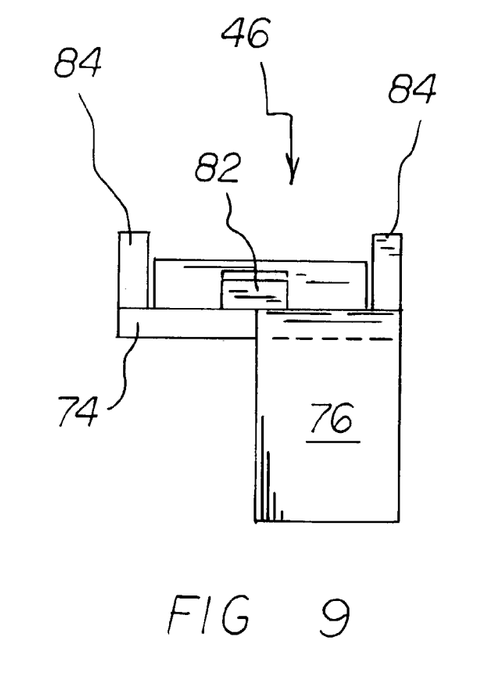
FIG. 9 is an end view of one of the inferior supports.
Figure 10:
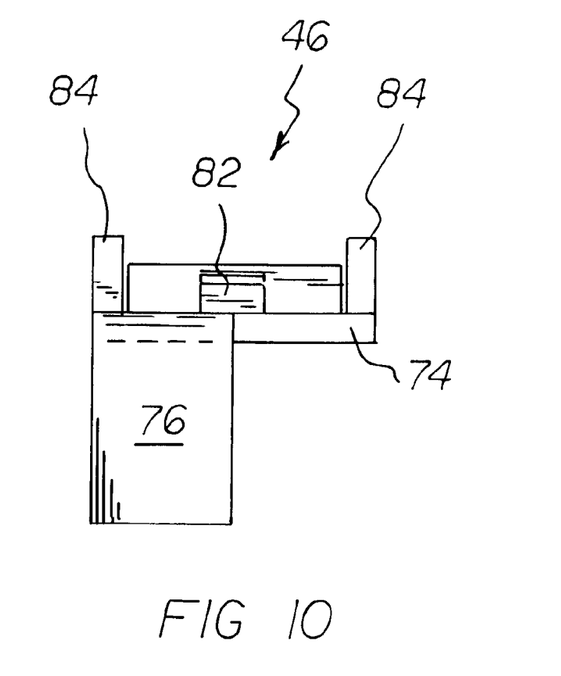
FIG. 10 is an end view of one of the inferior supports.

With reference now to FIGS. 9 through 10, the primary difference between the superior and inferior supports (44 and 46) will be described. That is, the lip 76 of the inferior support 46 is offset. More specifically, the lip portion 76 extends over only a portion of the width of the support 46. In the preferred embodiment depicted, the lip 76 extends over approximately half of the width of the support 46. As such, the lip portion 76 is offset to one side. Furthermore, with the support 46 positioned on the vertebrae, the adjacent lips 76 are preferably oriented toward the medial portion of the vertebrae. This offset lip portion 76 is contrasted to the lips 58 of the superior supports 44 which extend across the entire width of the support 44 (note FIG. 8). Thus, the lips 58 of the superior supports 44 are not offset.

Figure 13:
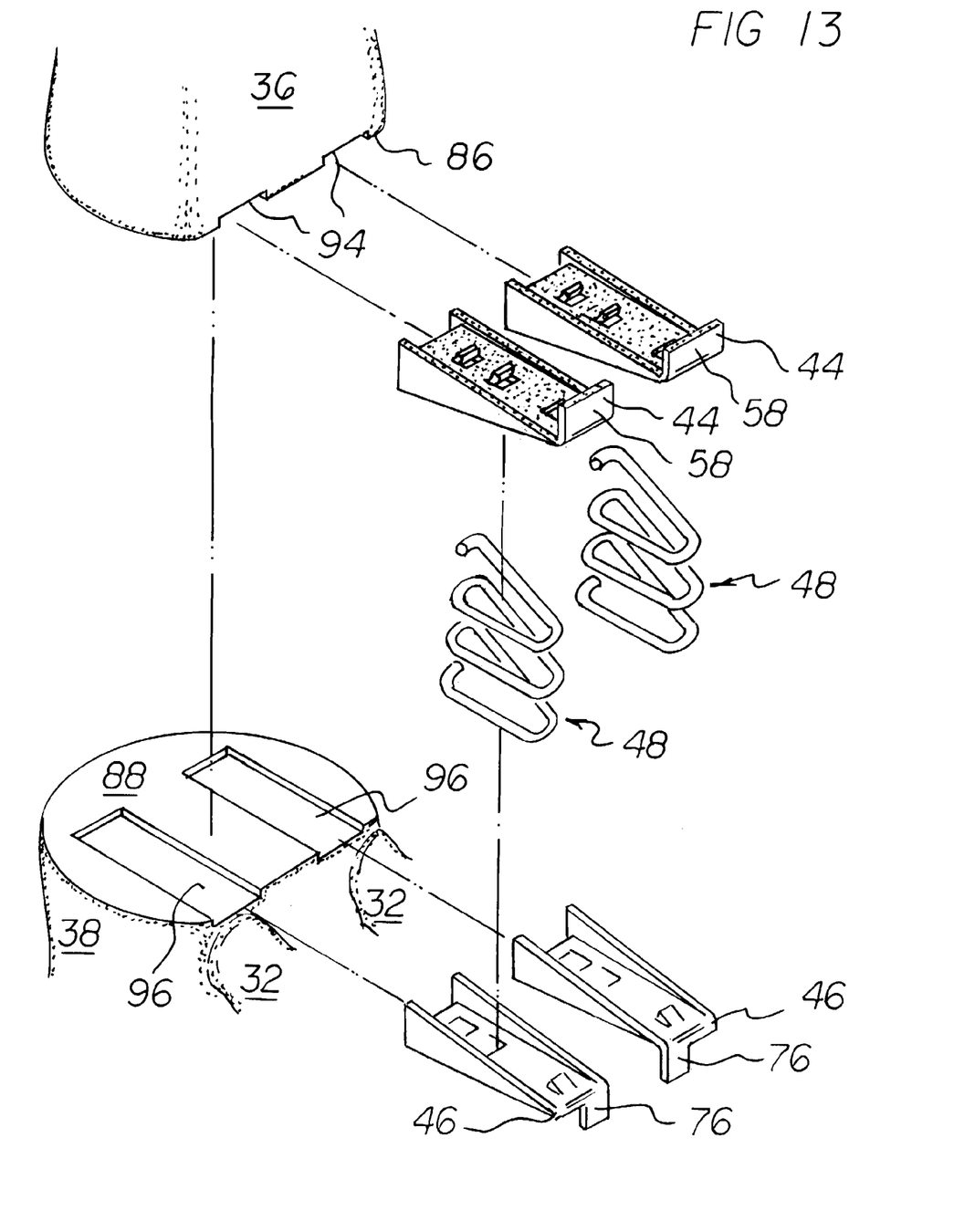
FIG. 13 is an exploded view of the implant system of the present invention.

The exact manner in which the supports (44 and 46) are positioned upon the facing surfaces of the opposing vertebrae is next described in conjunction with the exploded view of FIG. 13. As illustrated, the two superior supports 44 are secured to the surface 86 of the superior vertebrae 36, and the inferior supports 46 are secured to the facing surface 88 of the inferior vertebrae 38. More specifically, the two superior supports 44 are received within channels 92 that are formed within the inferior surface 86 of the superior vertebrae 36. These channels 92 are preferably formed after the medical practitioner has conducted the partial discectomy. The channels 92 are ideally dimensioned to specifically receive the width of the supports 44 and are relatively shallow when compared to the overall height of the support 44. The channels 92 aid in orienting the supports 44 and limiting their movement once positioned. After the channels 92 are formed the superior supports 44 are inserted over the surface 86 of the superior vertebrae 36. This is done with the teeth 62 and lips 58 directed toward the vertebral body. However, at this stage the teeth 62 do not engage the vertebral body 36, insomuch as the plate 56 is unbiased and the teeth 62 are flush with the lower surface of the support. As the supports 44 are pushed forward, the lip 58 of each support 44 will abut the posterior edge 94 of the vertebrae 36, which functions to properly orient the supports 44 relative to the vertebral body 36. That is, each lip 58 ensures that its corresponding support 44 does not extend too far onto the vertebral body 36.

The above described insertion is repeated for the inferior supports 46. That is, the inferior supports 46 are inserted within channels 96 formed within the facing superior surface 88 of the inferior vertebrae 38. Again, with the supports 46 inserted, the teeth 78 do not engage the vertebral body 38. After the discectomy, the inferior vertebrae 38 will have remaining pedicles 32 preventing insertion of a support with a full lip. Thus, the lower supports 46 include the offset lip 76 that accommodates the vertebral pedicle 32. Nonetheless, each offset lip 76 still functions in limiting the insertion of its corresponding support 46 into the corresponding channel 96.

Figure 11:
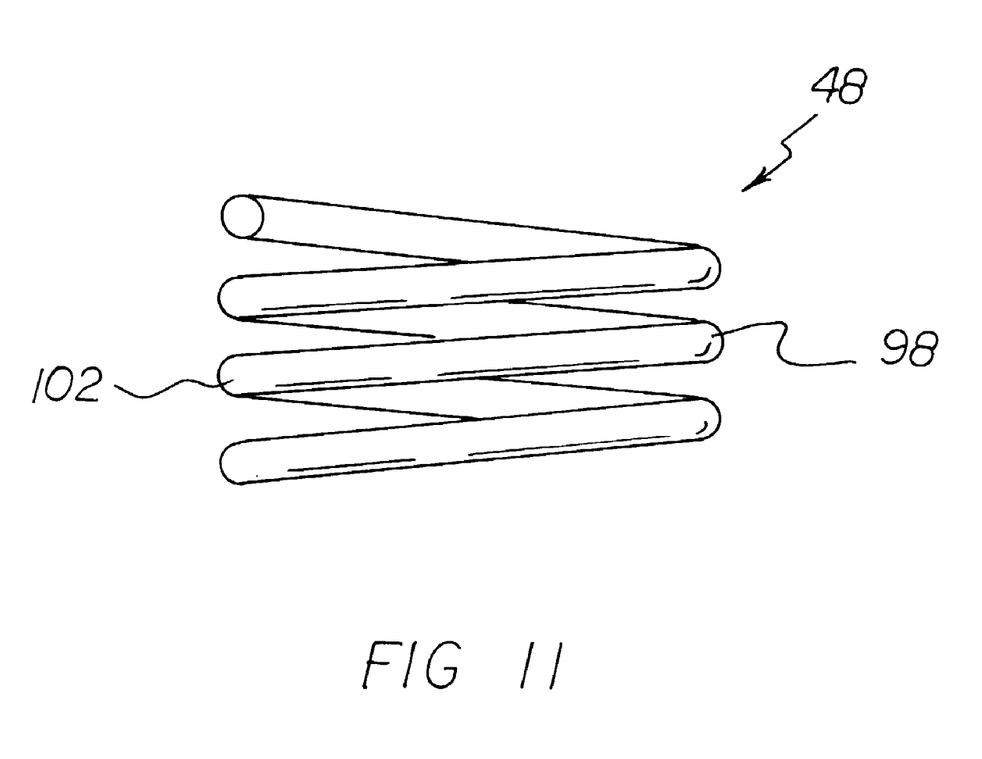
FIG. 11 is a side elevational view of one of the springs.
Figure 12:
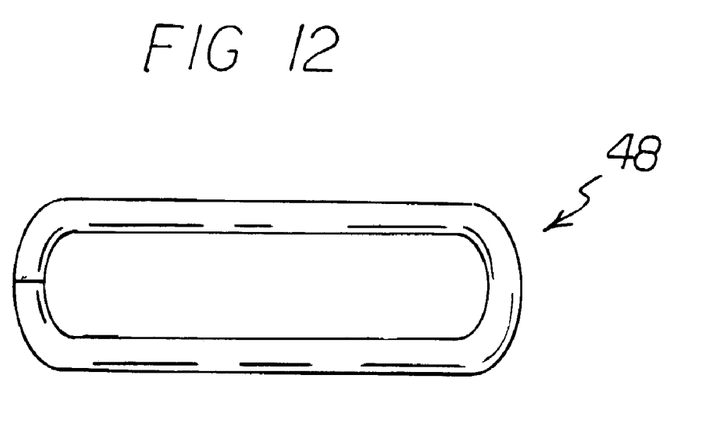
FIG. 12 is a plan view of one of the springs.

The implant further includes springs 48 which are engaged between the facing superior and inferior supports (44 and 46) as illustrated clearly in FIG. 13. Each support column 50 includes one spring 48, with two springs 48 being employed when two support columns 50 are used. In preferred embodiment, each of these springs 48 is a coil spring formed from a plurality of oblong coils. It has been found that the use of coil springs increases the life of the implant over elastomeric spring members. Preferably, each spring 48 is tapered from a second to a first end. This spring geometry is illustrated in FIG. 11. Furthermore, FIG. 12 is a plan view of the spring 48 showing its oblong or elongated shape. The resulting free-standing orientation of the spring provides a narrower posterior profile 98 and a wider anterior profile 102. This, in turn, insures that the spring 48, when inserted, provides proper spinal curvature.

With reference again to FIG. 13, the positioning of the springs 48 between the supports (44 and 46) is described. Specifically, each spring 48 is positioned such that the narrower end is adjacent the posterior edge of the spine and the wider end is adjacent the anterior edge of the spine. As indicated, this provides for proper spinal curvature with the implant fully inserted. Each of the springs 48 is held in place by opposing superior and inferior supports (44 and 46), and further by the upstanding side walls of such supports (66 and 84) and their retainer portions (64 and 82). More specifically, the side walls prevent the lateral movement of the spring 48 and the retainer (64 or 82) precludes the spring from moving longitudinally. When properly positioned, the springs 48 are under compression and generate an axial force that serves to pivot the cantilevered plates 56 and 74 away from their corresponding supports 44 and 46. As a consequence, the teeth 62 and 78 are forced into the vertebral bodies (36 and 38). This prevents any lateral migration of the supports. When fully positioned the springs absorb the forces between the superior and inferior vertebrae (36 and 38) and take the place of the otherwise existing fibrocartilage.

Method of Insertion

The method by which the implant of the present invention is inserted is next described. In the first step a partial discectomy is performed in order to gain posterior access to the damaged area. This discectomy involves removing the spinous process 22 and inferior articular process 26 from the superior vertebrae 36. The superior articular process 24 is also removed from the inferior vertebrae 38. This exposes the thecal sac, which is moved to gain access to the fibrocartilage. Next, the damaged fibrocartilage is removed to create an intervertebral space. This space provides access to the opposing vertebrae surfaces (86 and 88). Once the space is created the upper and lower channels (92 and 96) can be formed. Specifically, two oblong channels 92 are formed within the surface 86 of the superior vertebrae 36, and two oblong channels 96 are formed within the face 88 of the inferior vertebrae 38. These channels (92 and 96) are formed in facing relation to one another. Thereafter, the two superior supports 44 are inserted into the channels 92 with the lips 58 functioning to limit the insertion and otherwise properly orient the supports 44. The inferior supports 46 are then likewise positioned with the offset lips 76 engaging the remaining pedicles 32 on the inferior vertebrae 38. Lastly, the two springs 48 are inserted. More specifically, the first spring 48 is inserted intermediate the opposing superior and inferior supports (44 and 46) and the second spring 48 is inserted between the remaining opposing superior and inferior supports (44 and 46). In each instance, insertion of the spring causes the teeth to engage the vertebral body via action of the cantilevered plate.

Figure 14:
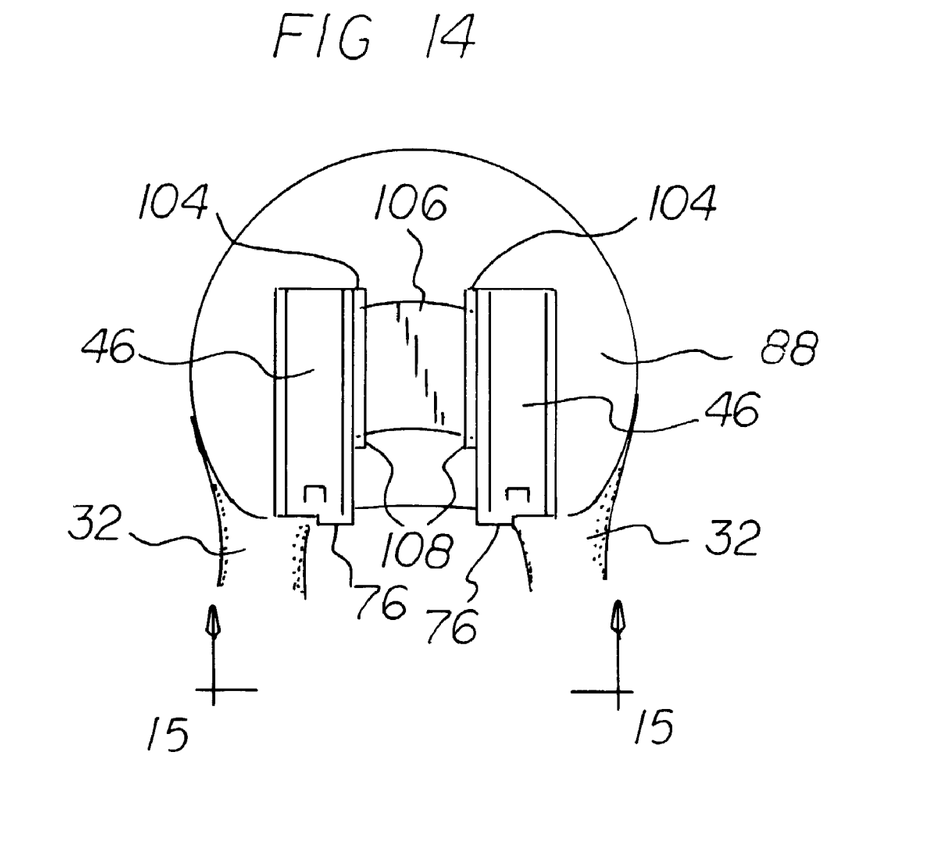
FIG. 14 is an alternative embodiment of the implant of the present invention.
Figure 15:
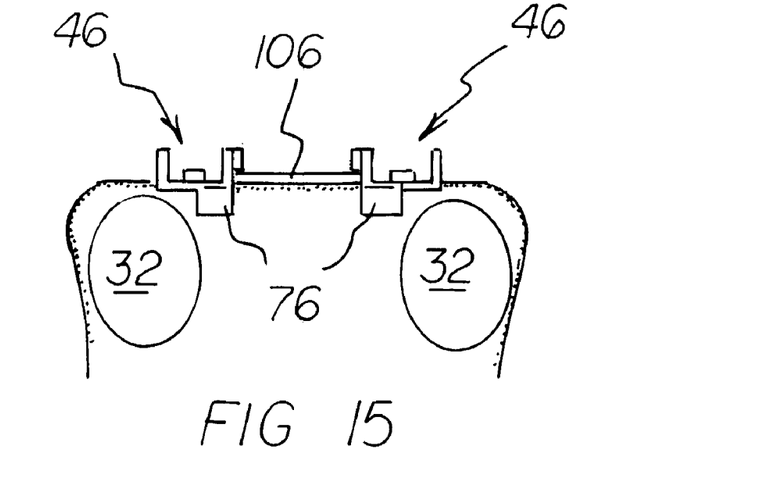
FIG. 15 is a view taken from line 15—15 of FIG. 14.
Figure 16:
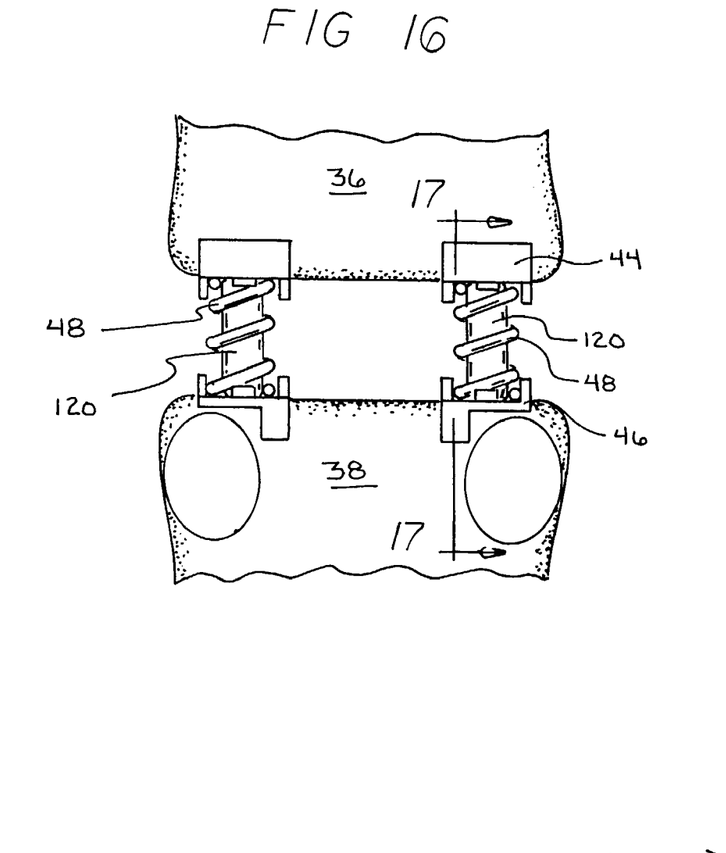
FIG. 16 is a detailed view taken from FIG. 1 of an alternative implant system of the present invention.

FIGS. 14 and 15 illustrate yet another embodiment of the present invention. This embodiment is similar in most respects to the previously described embodiment. However, the two inferior supports 46 are each provided with a channel 104 formed along an interior edge. These channels 104 are adapted to receive the sides of a spacer 106. That is, the opposing edges 108 of the spacer 106 are inserted within the facing channels 104 of the inferior supports 46. This spacer 106 operates to absorb any forces that would tend to operate individually on the supports 46. Consequently, the spacer 106 functions in tying the two supports 46 together such that they operate as an integral unit. The spacer 106 is preferably positioned intermediate the channels 104 prior to insertion over the vertebral body.

All of the components of the above-described invention, that is the superior and inferior supports (44 and 46), and the springs 48 as well as the spacer 106, are preferably formed from a titanium alloy or a stainless steel. Furthermore, each of these components is preferably coated with a hydroxyapatite to promote bone growth about the components when in place.

Alternative Embodiment

An alternative embodiment of the present invention is depicted in FIGS. 16–19. This alternative embodiment employs many of the same components discussed with reference to FIGS. 1 through 15, as such similar reference numerals are used to note similar components. However this alternative embodiment further includes two dampening matrices 120. Each matrix 120 utilizes an identical construction and is positioned between the superior and inferior supports (44 and 46) of the implant. The dampening matrices each act as a cushion between the adjacent superior and inferior lumbar vertebrae (36 and 38, respectively.) Accordingly, when the opposing vertebrae are compressed the matrices slow the rate of compression and absorb the forces and loads encountered by the spinal tract. As noted below, this is achieved by the hydrogel core 122 contained within each matrix.

Figure 17:
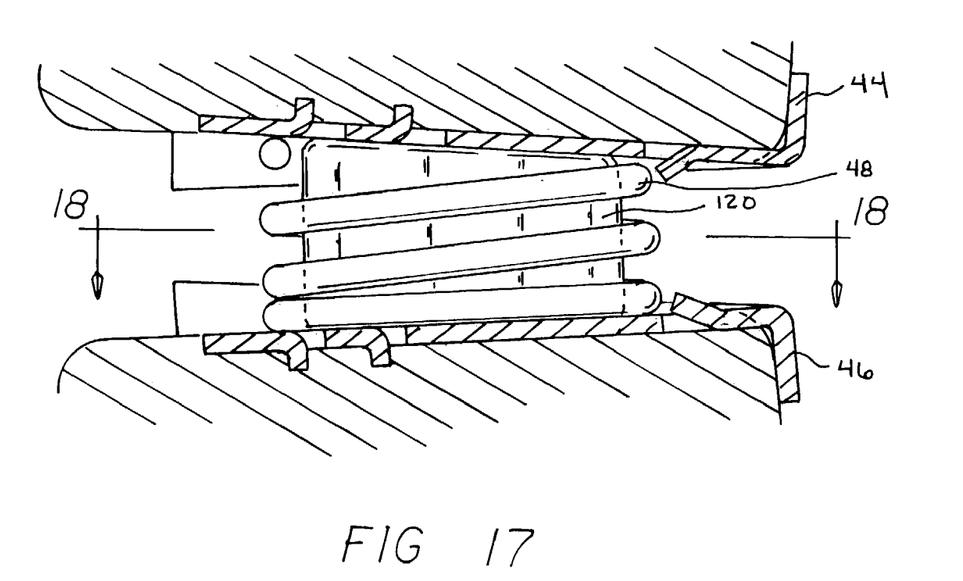
FIG. 17 is a side elevational view of alternative embodiment depicted in FIG. 16.
Figure 18:
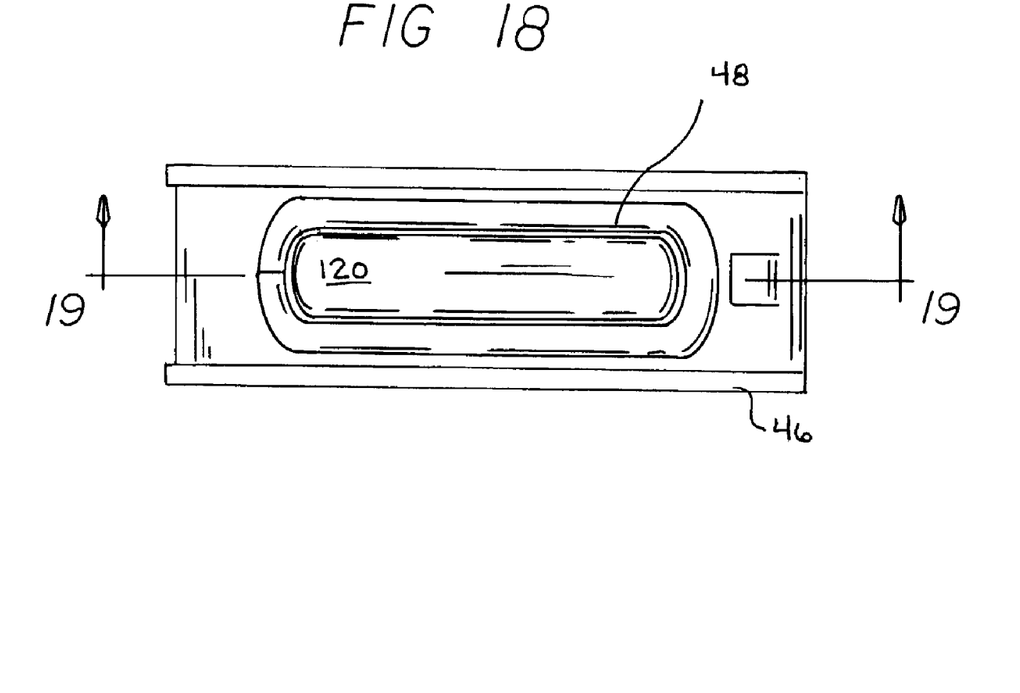
FIG. 18 is a top plan view taken along line 18—18 of FIG. 17.

Once the load is removed, resilient columns (or springs) provide a return energy to reposition the adjacent vertebrae. This repositioning is achieved in the absence of loads upon the vetebral tract. In the preferred embodiment, each of the resilient columns is positioned over and surrounds an associated dampening matrix. This arrangement is depicted in FIG. 17.

Figure 19:
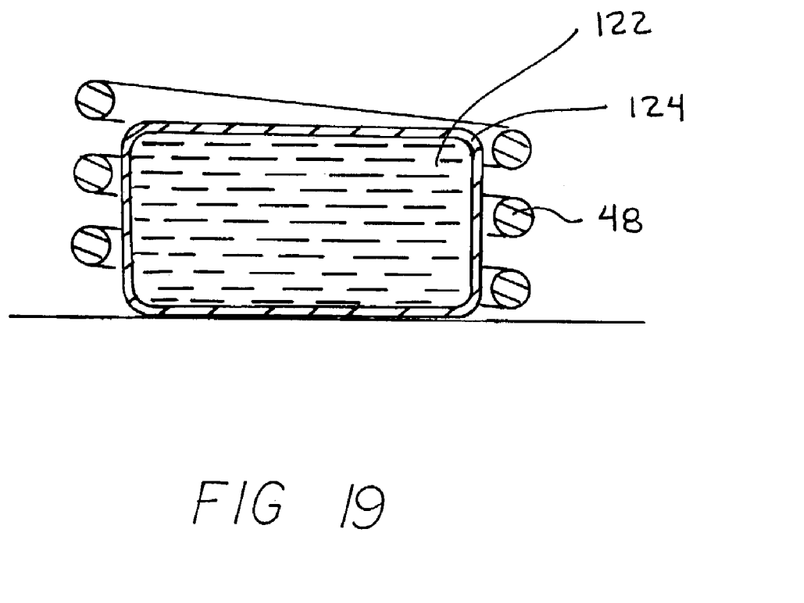
FIG. 19 is a sectional view taken along line 19—19 of FIG. 18.

In the preferred embodiment the dampening matrix constructed from a hydrogel core positioned within a constraining jacket. This construction is similar to the prosthetic spinal disc nucleus disclosed in U.S. Pat. No. 5,824,093 to Ray, the contents of which are incorporated herein by reference. As noted in Ray '093, the hydrogel core is formed as a mixture of hydrogel polyacrylonitrile. In particular, acrylamide and acrylonitrile are used. Furthermore the constraining jacket is preferably a closed sack of a tightly woven high molecular weight high tenacity polymerac fabric. The jacket preferably contains openings that are large enough to allow bodily fluids to react with the hydrogel core, but are small enough to prevent the hydrogel from escaping. Thus the hydrogel, which has an affinity for imbibing water, will deform and reform as necessary in order to accommodate and alleviate stresses and loads placed on the spinal tract. FIG. 19 is a cross sectional view illustrating the hydrogel core of the present invention.

After any loads applied to the hydrogel core are removed the resilient columns then return the opposing vertebrae to their proper orientation. In this regard, the preferred resilient column has been disclosed as a spring 48. However any other resilient tensioning devices known in the art can be employed. For example, the column can be formed from a leaf spring, coil spring, resilient coiled polymer or a continuous polymer sleeve.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

The invention claimed is:

1. A vertebral implant device for insertion between upper and lower vertebral surfaces comprising:
   an upper plate;
   a lower plate;
   a helical coil spring connecting said upper plate to said lower plate, wherein said helical coil spring defines an inner annular space;
   a flexible dampening matrix positioned within said inner annular space of said helical coil spring comprising a flexible constraining jacket surrounding a flexible core.

2. The vertebral implant device of claim 1 wherein said upper plate includes a plurality of teeth disposed upwardly and said lower plate includes a plurality of teeth disposed downwardly.

3. The vertebral implant device of claim 1 wherein said upper and lower plates each include sidewalls to hold said spring in a fixed position.

4. The vertebral implant device of claim 3 wherein one or more of said sidewalls are tapered.

5. The vertebral implant device of claim 1 wherein said flexible dampening matrix core is formed from hydrogel.

6. The vertebral implant device of claim 5 wherein said flexible dampening matrix constraining jacket has openings that are large enough to allow fluids to react with the hydrogel core, but are small enough to prevent the hydrogel from escaping.

7. The vertebral implant device of claim 1 wherein said flexible dampening matrix constraining jacket comprises a closed sack of a tightly woven polymeric fabric.

8. A surgical method for replacing damaged fibrocartilage between facing superior and inferior vertebrae in the lumbar region of a patient's spine comprising the steps of:

accessing the facing superior and inferior vertebrae through the posterior region of the patient;

performing a partial discectomy in order to gain access to the damaged fibrocartilage;

removing the damaged fibrocartilage to create an intervertebral space between facing superior and inferior vertebrae surfaces;

inserting a vertebral implant device into said intervertebral space between said facing superior and inferior vertebrae surfaces wherein said vertebral implant device comprises an upper plate, a lower plate, a helical coil spring connecting said upper plate to said lower plate and defining an inner annular space, and a flexible dampening matrix positioned within said inner annular space including a flexible constraining jacket surrounding a flexible core.

9. The surgical method of claim 8 further comprising the steps of forming channels on the facing superior and inferior vertebrae surfaces and attaching said upper and lower plates of said vertebral implant device to said channels.

10. The surgical method of claim 9 wherein a pair of vertebral implant devices are inserted into side-by-side channels on said facing superior and inferior vertebrae surfaces.

* * * * *